United States Patent

Meiers et al.

[11] Patent Number: 5,688,123
[45] Date of Patent: Nov. 18, 1997

[54] TRANSFER CAP FOR DENTAL IMPLANTS

[75] Inventors: Willi Meiers, Alzenau; Thomas Lange, Langenselbold; Werner Groll, Alzenau, all of Germany

[73] Assignee: Degussa Aktiengesellschaft, Frankfurt, Germany

[21] Appl. No.: 434,688

[22] Filed: May 4, 1995

[30] Foreign Application Priority Data

May 4, 1994 [DE] Germany .................. 44 15 670.7

[51] Int. Cl.$^6$ ............................................. A61C 8/00
[52] U.S. Cl. .......................... 433/173; 433/172; 433/214
[58] Field of Search ................................. 433/172, 173, 433/174, 175, 176, 214

[56] References Cited

U.S. PATENT DOCUMENTS

| | | | |
|---|---|---|---|
| 5,026,285 | 6/1991 | Durr et al. | 433/173 |
| 5,195,891 | 3/1993 | Sulc | 433/173 |
| 5,259,759 | 11/1993 | Jorneus et al. | 433/173 |
| 5,302,125 | 4/1994 | Kownacki et al. | 433/172 |
| 5,368,483 | 11/1994 | Sutter et al. | 433/173 |
| 5,417,570 | 5/1995 | Zuest et al. | 433/172 X |

*Primary Examiner*—Nicholas D. Lucchesi
*Attorney, Agent, or Firm*—Beveridge, DeGrandi, Weilacher & Young LLP

[57] ABSTRACT

A transfer cap for dental implants which is protected during the working in the mouth against rotations and shifting and therefore permits a precise molding of the oral situation, carries one or more resilient flaps on its open end and is optionally provided with protuberances.

8 Claims, 1 Drawing Sheet

TRANSFER CAP FOR DENTAL IMPLANTS

INTRODUCTION AND BACKGROUND

The present invention relates to a transfer cap for dental implants with a tapered formed inner surface opening to the implant wherein the inner surface is adapted in form and in size to the built-up part of the implant.

Recently, dental implants have been increasingly employed which are inserted or implanted into the jawbone of a patient at the site of missing natural teeth so that a denture, or dental prosthesis can be fixed onto them (FIG. 3, element 7). These implants usually consist of two parts, an endosseous part to be screwed into the jawbone and a built-up part or abutment which can be screwed into the endosseous part and which is usually conically designed on the end opposite the endosseous part. The denture is fixed onto this tapered part. Such implants are well known in the art and are described for example in DE-PS 40 35 172 (which is incorporated by reference in its entirety).

For taking care of patients with artificial dentures, as a rule, prefabricated built-up parts are used which are screwed into the endosseous part. These built-up parts or abutments serve as a base for the production of firmly fixed dentures which can be removed or conditionally removed. In contrast to the impression of prepared teeth, in this instance the oral situation can be transferred with ready-made parts to a dental model. So-called transfer caps are used for this which are placed on the built-up part or abutment and remain in the impression material (e.g. silicon, polyether) after the taking of the impression. The dental technician then places the laboratory analog of the built-up part into the transfer cap and produces the master model.

Very different transfer caps are used to produce the impression. Thus, there are transfer caps which can be set without further fastening onto the built-up implant part. A disadvantage of this technique is the fact that due to the loose seat of the transfer cap on the built-up part during the impression or also during the following production of the model, inaccuracies can arise as a result of rotation or shifting of the transfer cap or of the laboratory analog.

A much more precise type of impression involves producing an individual impression tray which is perforated above the implant. The transfer cap can then be fastened onto the built-up part through this perforation by means of a fastening screw. After the impression material has hardened the screw projecting into the buccal cavity through the perforation of the impression tray is loosened and the impression can be removed. Then, in order to produce the master model, the laboratory analog is placed in accordance with the procedure indicated above into the impression cap which is located in the impression compound and is screwed again through the perforation of the individual impression tray. The plaster model is then produced. A significant disadvantage of these methods is the fact that the expense for achieving a precise molding is very high since at first an individual tray must be produced and, in addition, the screwing into the jawbone can be expensive and problematic, especially in hard-to-reach areas.

SUMMARY OF THE INVENTION

One object of the present invention therefore was to solve the problem of constructing a transfer cap for dental implants with a tapered formed inner surface opening in the direction of the implant which cap is adapted in form and size to the built-up part or abutment of the implant and which permits a precise impression in the oral cavity without great expense.

The invention solves this problem in that the transfer cap carries one or more resilient flaps or tongues on its open end which extend in the inserted state over the shoulders 9 of the conical area of the built-up part. The transfer cap is advantageously additionally provided with one or more indentations 5 or slots around its outer circumferential surface. These indentations or slots which are arranged at regular intervals can optionally clamp or engage into corresponding recesses 10 formed into the built-up part 8.

BRIEF DESCRIPTION OF THE DRAWINGS

The present invention will be further understood with reference to the drawings, wherein.

DETAILED DESCRIPTION OF THE INVENTION

The transfer cap is fixed on the built-up part via the resilient flaps and optionally by way of the indentations or slots. This fixing permits a precise molding of the oral situation without an undesired rotation or vertical shifting of the transfer cap out of the proper position taking place during the working production of the model.

Figure 1:
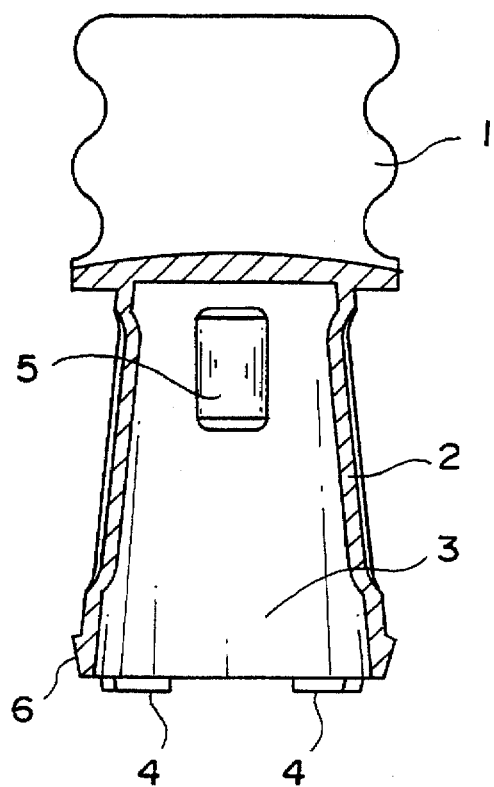
FIGS. 1 and 2 schematically show an exemplary embodiment of a transfer cap in a partial elevation cross section and sectional top view, respectively.
Figure 2:
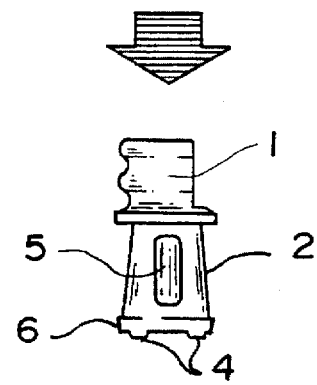
Figure 2:
Figure 2:
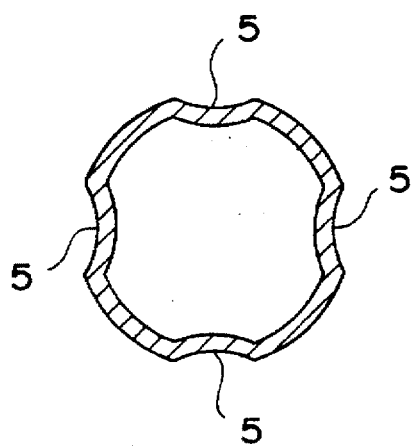
Figure 3:
FIG. 3 shows the transfer cap in reference to the dental implant.

FIGS. 1 and 2 schematically show an exemplary embodiment of a transfer cap in a partial elevation cross section and sectional top view, respectively. The cylindrical transfer cap 1 is of a generally tapered formation, at least in its lower part 2. The conical section tapers to the base 6 which is of larger diameter than the top portion of the conical section. The form and size of conical hollow space 3 of transfer cap 1 corresponds to the form and size of the conical area of the built-up part of the dental implant (FIG. 3, element 8). This transfer cap 1 is provided on its open base end with one or more resilient flaps 4 which extend in the inserted state over the shoulders 9 of the conical area of the built-up part and thus reliably prevent a vertical shifting, and also in part a rotation of transfer cap 1 on the built-up part. In addition, transfer cap 1 can also be provided with a plurality of indentations or slots 5 which form protuberances on an inner chamber wall which make possible an additional protection against rotation. The transfer cap can be easily separated from the built-up part by means of a vertical traction force (FIG. 3).

The transfer cap is made of metal, preferably aluminum alloy, though is can also be made of synthetic material such as plastic.

Further variations and modifications of the foregoing will be apparent to those skilled in the art and such variations and modifications are intended to be encompassed by the claims that are appended hereto.

German Priority Application P 44 15 670.7, filed on May 4, 1994 is relied on and incorporated by reference.

We claim:

1. A transfer cap for dental implants, comprising:
   an upper portion and a lower portion, wherein said lower portion further comprises,
   a top portion and a bottom portion with a base end, an outer surface and an inner surface, said inner surface being of a tapered conical shape and forming a conical chamber with a conical inner chamber wall open at the base end and wherein said inner chamber wall has protuberance that communicate with corresponding recesses of a dental implant when said lower portion engages the dental implant by receiving the dental implant in said chamber.

2. A transfer cap as described in claim 1, wherein:

the diameter of said conical chamber is larger at the base end than the diameter of said conical chamber at the top portion.

3. A transfer cap for dental implants, comprising:

an upper portion and a lower portion, wherein said lower portion further comprises, a top portion and a bottom portion with a base end, an outer surface and an inner surface, said inner surface being of a tapered conical shape and forming a conical chamber open at the base end, wherein said lower portion engages a dental implant by receiving the dental implant in said chamber when the transfer cap is engaged with a dental implant and wherein said base end is provided with one or more resilient flaps which grasp the dental implant when the dental implant is engaged by said transfer cap.

4. A transfer cap as described in claim 3, wherein:

the diameter of said conical chamber is larger at the base end than the diameter of said conical chamber at the top portion.

5. A transfer cap as described in claim 3 or 4, wherein the said transfer cap is made of aluminum alloy.

6. A transfer cap as described in claim 3 or 4, wherein the said transfer cap is made of plastic.

7. A transfer cap as described in claim 3 wherein;

said inner surface of said conical chamber has protuberances that engage corresponding recesses of the dental implant.

8. A transfer cap as described in claim 4 wherein;

said inner surface of said conical chamber has protuberances that engage corresponding recesses of the dental implant.

* * * * *